US012740992B2

(12) United States Patent
Checketts et al.

(10) Patent No.: US 12,740,992 B2

(45) Date of Patent: Sep. 22, 2026

(54) USE OF CANNABIDIOL IN THE TREATMENT OF SEIZURES ASSOCIATED WITH RARE EPILEPSY SYNDROMES RELATED TO GENETIC ABNORMALITIES

(71) Applicant: Jazz Pharmaceuticals Research UK Limited, Sittingbourne (GB)

(72) Inventors: Daniel Adam Checketts, Sittingbourne (GB); Kevin James Craig, Sittingbourne (GB)

(73) Assignee: Jazz Pharmaceuticals Research UK Limited, Sittingbourne (GB)

( * ) Notice: Subject to any disclaimer, the term of this patent is extended or adjusted under 35 U.S.C. 154(b) by 716 days.

(21) Appl. No.: 18/006,121

(22) PCT Filed: Jul. 15, 2021

(86) PCT No.: PCT/EP2021/069834

§ 371 (c)(1),
(2) Date: Jan. 19, 2023

(87) PCT Pub. No.: WO2022/017926

PCT Pub. Date: Jan. 27, 2022

(65) Prior Publication Data

US 2023/0285426 A1 Sep. 14, 2023

(30) Foreign Application Priority Data

Jul. 20, 2020 (GB) ..................................... 2011127

(51) Int. Cl.

| | |
|---|---|
| ***A61K 31/00*** | (2006.01) |
| ***A61K 31/195*** | (2006.01) |
| ***A61K 31/4015*** | (2006.01) |
| ***A61K 31/4166*** | (2006.01) |
| ***A61K 31/551*** | (2006.01) |
| ***A61K 31/7028*** | (2006.01) |
| ***A61P 25/12*** | (2006.01) |

(52) U.S. Cl.

CPC .......... *A61K 31/658* (2023.05); *A61K 31/195* (2013.01); *A61K 31/4015* (2013.01); *A61K 31/4166* (2013.01); *A61K 31/551* (2013.01); *A61K 31/7028* (2013.01); *A61P 25/12* (2018.01)

(58) Field of Classification Search

CPC .. A61K 2300/00; A61K 31/05; A61K 31/195; A61K 31/4015; A61K 31/4166; A61K 31/551; A61K 31/658; A61K 31/7028; A61K 31/7048; A61K 45/06; A61P 25/08; A61P 25/12

See application file for complete search history.

(56) References Cited

U.S. PATENT DOCUMENTS

| | | | |
|---|---|---|---|
| 8,632,825 | B2 | 1/2014 | Velasco Diez et al. |
| 8,790,719 | B2 | 7/2014 | Parolaro et al. |
| 9,017,737 | B2 | 4/2015 | Kikuchi et al. |
| 9,125,859 | B2 | 9/2015 | Whalley et al. |
| 9,474,726 | B2 | 10/2016 | Guy et al. |
| 9,675,654 | B2 | 6/2017 | Parolaro et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 9,962,341 | B2 | 5/2018 | Stott et al. |
| 10,039,724 | B2 | 8/2018 | Stott et al. |
| 10,092,525 | B2 | 10/2018 | Guy et al. |
| 10,098,867 | B2 | 10/2018 | Javid et al. |
| 10,111,840 | B2 | 10/2018 | Guy et al. |
| 10,137,095 | B2 | 11/2018 | Guy et al. |
| 10,220,005 | B2 | 3/2019 | Martinez-Orgado et al. |
| 10,226,433 | B2 | 3/2019 | Di Marzo et al. |
| 10,583,096 | B2 | 3/2020 | Guy et al. |
| 10,603,288 | B2 | 3/2020 | Guy et al. |
| 10,653,641 | B2 | 5/2020 | Robson et al. |
| 10,709,671 | B2 | 7/2020 | Guy et al. |
| 10,709,673 | B2 | 7/2020 | Guy |
| 10,709,674 | B2 | 7/2020 | Guy et al. |
| 10,729,665 | B2 | 8/2020 | Whalley et al. |
| 10,758,514 | B2 | 9/2020 | Liu et al. |
| 10,765,643 | B2 | 9/2020 | Guy et al. |
| 10,799,467 | B2 | 10/2020 | Whalley et al. |
| 10,807,777 | B2 | 10/2020 | Whittle |
| 10,849,860 | B2 | 12/2020 | Guy et al. |

(Continued)

FOREIGN PATENT DOCUMENTS

| | | | |
|---|---|---|---|
| GB | 2531280 | A | 4/2016 |
| WO | WO-2019045121 | A1 | 3/2019 |

(Continued)

OTHER PUBLICATIONS

Deacon, H., "The fight for getting access to medical cannabis in the UK goes on," Aug. 23, 2019, 8 pages; https://www.healtheuropa.eu/access-to-medical-cannabis-in-the-uk/93025/.

(Continued)

*Primary Examiner* — Savitha M Rao

(74) *Attorney, Agent, or Firm* — COOLEY LLP

(57) ABSTRACT

The present invention relates to the use of cannabidiol (CBD) for the treatment of seizures associated with rare epilepsy syndromes. In particular the seizures associated with rare epilepsy syndromes that are treated are those which are experienced inpatients diagnosed with PCDH19 Epilepsy. In a further embodiment the types of seizures include tonic-clonic seizures. Preferably the dose of CBD is between 5 mg/kg/day to 50 mg/kg/day.

13 Claims, No Drawings

(56) References Cited

U.S. PATENT DOCUMENTS 10,918,608 B2 2/2021 Guy et al.
10,966,939 B2 4/2021 Guy et al.
11,000,486 B2 5/2021 Wright et al.
11,065,209 B2 7/2021 Guy et al.
11,065,227 B2 7/2021 Stott et al.
11,096,905 B2 8/2021 Guy et al.
11,147,776 B2 10/2021 Stott et al.
11,147,783 B2 10/2021 Stott et al.
11,154,516 B2 10/2021 Guy et al.
11,154,517 B2 10/2021 Guy et al.
11,160,757 B1 11/2021 Wilkhu et al.
11,160,795 B2 11/2021 Guy et al.
11,207,292 B2 12/2021 Guy et al.
11,229,612 B2 1/2022 Wright et al.
11,291,631 B2 4/2022 Shah
11,311,498 B2 4/2022 Guy et al.
11,318,109 B2 5/2022 Whalley et al.
11,357,741 B2 6/2022 Guy et al.
11,400,055 B2 8/2022 Guy et al.
11,406,623 B2 8/2022 Guy et al.
11,413,266 B2 8/2022 Biróet al.
11,419,829 B2 8/2022 Whalley et al.
11,426,362 B2 8/2022 Wright et al.
11,446,258 B2 9/2022 Guy et al.
11,590,087 B2 2/2023 Guy et al.
11,633,369 B2 4/2023 Guy et al.
11,679,087 B2 6/2023 Guy et al.
11,684,598 B2 6/2023 Stott et al.
11,701,330 B2 7/2023 Guy et al.
11,766,411 B2 9/2023 Guy et al.
11,793,770 B2 10/2023 Stott et al.
11,806,319 B2 11/2023 Wilkhu et al.
2015/0359756 A1 12/2015 Guy et al.
2017/0239193 A1 8/2017 Guy et al.
2018/0071210 A1 3/2018 Wilkhu et al.
2018/0228751 A1 8/2018 Stott et al.
2019/0167583 A1 6/2019 Shah
2019/0247333 A1 8/2019 Farfel et al.
2019/0314296 A1 10/2019 Wright et al.
2019/0321307 A1 10/2019 Guy et al.
2019/0365667 A1 12/2019 Wright et al.
2020/0138738 A1 5/2020 Guy et al.
2020/0179303 A1 6/2020 Guy et al.
2020/0206153 A1 7/2020 Whalley et al.
2020/0237683 A1 7/2020 Whalley et al.
2020/0297656 A1 9/2020 Guy et al.
2020/0352878 A1 11/2020 Guy et al.
2021/0015789 A1 1/2021 Guy et al.
2021/0052512 A1 2/2021 Guy et al.
2021/0059949 A1 3/2021 Wilkhu et al.
2021/0059960 A1 3/2021 Wilkhu et al.
2021/0059976 A1 3/2021 Wilkhu et al.
2021/0069333 A1 3/2021 Velasco Diez et al.
2021/0100755 A1 4/2021 Whalley et al.
2021/0169824 A1 6/2021 Guy et al.
2021/0177773 A1 6/2021 Guy et al.
2021/0290565 A1 9/2021 Guy et al.
2021/0308072 A1 10/2021 Wright et al.
2021/0330636 A1 10/2021 Guy et al.
2021/0401771 A1 12/2021 Guy et al.
2022/0000800 A1 1/2022 Guy et al.
2022/0008355 A1 1/2022 Guy et al.
2022/0016048 A1 1/2022 Guy et al.
2022/0023232 A1 1/2022 Guy et al.
2022/0040155 A1 2/2022 Guy et al.
2022/0062197 A1 3/2022 Stott et al.
2022/0062211 A1 3/2022 Stott et al.
2022/0087951 A1 3/2022 Knappertz
2022/0096397 A1 3/2022 Wright et al.
2022/0168266 A1 6/2022 Guy et al.
2022/0183997 A1 6/2022 Guy et al.
2022/0184000 A1 6/2022 Guy et al.
2022/0202738 A1 6/2022 Guy et al.
2022/0211629 A1 7/2022 Wilkhu et al.
2022/0226257 A1 7/2022 Guy et al.
2022/0233495 A1 7/2022 Silcock et al.
2022/0249396 A1 8/2022 Guy et al.
2022/0257529 A1 8/2022 Guy et al.
2022/0265573 A1 8/2022 Guy et al.
2022/0288055 A1 9/2022 Silcock et al.
2022/0378714 A1 12/2022 Guy et al.
2022/0378715 A1 12/2022 Guy et al.
2022/0378738 A1 12/2022 Guy et al.
2022/0387347 A1 12/2022 Whalley et al.
2022/0395470 A1 12/2022 Whalley et al.
2022/0395471 A1 12/2022 Guy et al.
2023/0000789 A1 1/2023 Guy et al.
2023/0022487 A1 1/2023 Guy et al.
2023/0024312 A1 1/2023 Whalley et al.
2023/0026079 A1 1/2023 Guy et al.
2023/0032502 A1 2/2023 Guy et al.
2023/0038423 A1 2/2023 Silcock et al.
2023/0068885 A1 3/2023 Guy et al.
2023/0143812 A1 5/2023 Knappertz et al.
2023/0235825 A1 7/2023 Thompson et al.
2023/0248664 A1 8/2023 Guy
2023/0263744 A1 8/2023 Guy
2023/0277560 A1 9/2023 Checketts et al.
2023/0277561 A1 9/2023 Checketts et al.
2023/0277562 A1 9/2023 Checketts et al.
2023/0277563 A1 9/2023 Checketts et al.
2023/0285419 A1 9/2023 Checketts et al.
2023/0285420 A1 9/2023 Checketts et al.
2023/0285421 A1 9/2023 Checketts et al.
2023/0285422 A1 9/2023 Checketts et al.
2023/0285423 A1 9/2023 Checketts et al.
2023/0285424 A1 9/2023 Checketts et al.
2023/0285425 A1 9/2023 Checketts et al.
2023/0285427 A1 9/2023 Checketts et al.
2023/0285428 A1 9/2023 Checketts et al.
2023/0301934 A1 9/2023 Whalley et al.
2023/0301936 A1 9/2023 Guy
2023/0310464 A1 10/2023 Checketts et al.

FOREIGN PATENT DOCUMENTS

WO WO-2019071302 A1 4/2019
WO WO-2019207319 A1 10/2019
WO WO-2020161083 A1 8/2020

OTHER PUBLICATIONS

Devinsky, O. et al., "Cannabidiol in patients with treatment-resistant epilepsy: an open-label interventional trial," The Lancet Neurology, Published online; Dec. 23, 2015; 9 pages; doi:https://doi.org/10.1016/S1474-4422(15)00379-8.

Devinsky, O. et al., "Trial of Cannabidiol for Drug-Resistant Seizures in the Dravet Syndrome," N Engl J Med, 376(21):2011-2020 (2017).

Eadie, M. J., "Shortcomings in the current treatment of epilepsy," Expert Rev Neurother., 12(12):1419-1427 (2012).

Elsohly, M. & Gul, W., Handbook of Cannabis, Chapter 1, Constituents of Cannabis Sativa, Roger Pertwee, Ed., 2012, 21 pages.

EPIDIOLEX® (cannabidiol) oral solution, CV, Prescribing Information, 2018, 30 pages; https://www.accessdata.fda.gov/drugsatfda_docs/label/2018/210365lbl.pdf.

Hausman-Kedem, M. et al., "Efficacy of CBD-enriched medical cannabis for treatment of refractory epilepsy in children and adolescents—An observational, longitudinal study," Brain Dev., 40(7):544-551 (2018); doi:10.1016/j.braindev.2018.03.013. Epub Apr. 16, 2018.

Hess, E. J. et al., "Cannabidiol as a new treatment for drug-resistant epilepsy in tuberous sclerosis complex," Epilepsia, 57(10):1617-1624 (2016); doi:10.1111/epi.13499.

Kurian, M. et al., "Focal cortical malformations in children with early infantile epilepsy and PCDH19 mutations: case report," Developmental Medicine & Child Neurology, 60(1):100-105 (2018); doi:10.1111/dmcn.13595. Epub Oct. 24, 2017.

Kwan, P. et al., "Definition of drug resistant epilepsy: consensus proposal by the ad hoc Task Force of the ILAE Commission on

(56) References Cited

OTHER PUBLICATIONS

Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.
Oppenheim, M., "Government refuses medical cannabis to six-year-old epileptic boy who had 3,000 seizures in a year," Feb. 18, 2018, 6 pages; https://www.independent.co.uk/news/uk/home-news/alfie-dingley-home-office-medical-cannabis-denies-seizures-netherlands-a8216596.html.
Pertwee, R. G., "The Pharmacology and Therapeutic Potential of Cannabidiol," Cannabinoids, Chapter 3, DiMarzo, V. (Ed.), pp. 32-83 (2004).
Porter, B. E. & Jacobson, C., "Report of a parent survey of cannabidiol-enriched cannabis use in pediatric treatment-resistant epilepsy," Epilepsy Behav., 29(3):574-577 (2013).
Rosenberg, E. C. et al., "Quality of Life of Childhood Epilepsy (QOLCE) in pediatric patients enrolled in a prospective, open-label clinical study with cannabidiol (CBD)," Epilepsia, 58(8):e96-e100 (2017); doi:10.1111/epi.13815.
Thiele, E. et al., "Cannabidiol in patients with Lennox-Gastaut syndrome: Interim analysis of an open-label extension study," Epilepsia, 60:419-428 (2019).
Thurman, D. J. et al., "Standards for epidemiologic studies and surveillance of epilepsy," Epilepsia, 52 (Suppl 7):2-26 (2011).
U.S. Appl. No. 15/640,033, filed Jun. 30, 2017.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/472,000, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/552,487, filed Dec. 16, 2021.
U.S. Appl. No. 17/576,868, filed Jan. 14, 2022.
U.S. Appl. No. 17/585,485, filed Jan. 26, 2022.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/817,753, filed Aug. 5, 2022.
U.S. Appl. No. 17/853,367, filed Jun. 29, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18/006,131, filed Jan. 19, 2023.
U.S. Appl. No. 18/006,133, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/320,906, filed May 19, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
U.S. Appl. No. 18/477,467, filed Sep. 28, 2023.
U.S. Appl. No. 18/479,671, filed Oct. 2, 2023.
U.S. Appl. No. 18/560,316, filed Nov. 10, 2023.
U.S. Appl. No. 18/560,337, filed Nov. 10, 2023.
U.S. Appl. No. 18/560,341, filed Nov. 10, 2023.
U.S. Appl. No. 18/560,346, filed Nov. 10, 2023.
Chiron, C. & Dulac, O., "The pharmacologic treatment of Dravet syndrome," Epilepsia, 52(Suppl 2):72-5 (Apr. 2011).
Dulac, O. & Kaminska, A., "Use of Lamotrigine in Lennox-Gastaut and Related Epilepsy Syndromes," J. Child Neurolog., 12(Suppl 1): S23-S29 (Nov. 1997).
Kelley, S. A. & Kossoff, E. H., "Doose syndrome (myoclonic-astatic epilepsy): 40 years of progress," Developmental Med. & Child Neurol., 52(11):988-93 (Nov. 2010).
Lutz, B., "On-demand activation of the endocannabinoid system in the control of neuronal excitability and epileptiform seizures." Biochemical Pharmacology 68: 1691-1698 (Nov. 2004).
Mayo Clinic, "Carbamazepine (oral route)," [drug information], provided by Merative, Micromedex®, DRG-20062739, (initial publication date unknown; last updated Feb. 1, 2026). [Accessed Feb. 12, 2026, publicly available at URL: https://www.mayoclinic.org/drugs-supplements/carbamazepine-oral-route/description/drg-20062739], 28 pages.
Mayo Clinic, "Phenytoin (oral route)," [drug information], provided by Merative, Micromedex®, DRG-20072875, (initial publication date unknown; last updated Feb. 1, 2026). [Accessed Feb. 12, 2026, publicly available at URL: https://www.mayoclinic.org/drugs-supplements/phenytoin-oral-route/description/drg-20072875], 24 pages.
Mayo Clinic, "Vigabatrin (oral route)," [drug information], provided by Merative, Micromedex®, DRG-20066675, (initial publication date unknown, last updated Feb. 1, 2026). [Accessed Mar. 2, 2026, publicly available at URL: https://www.mayoclinic.org/drugs-supplements/vigabatrin-oral-route/description/drg-20066675], 19 pages.
U.S. Food and Drug Administration, "What We Do," [website] FDA.gov., U.S. Department of Health and Human Services, (initial publication unknown; last updated Nov. 21, 2023). [Accessed Feb. 12, 2026, publicly available at URL: https://www.fda.gov/about-fda/what-we-do], 5 pages.

(56) References Cited

OTHER PUBLICATIONS

Vossler, D. G. & Gidal, B. E., "A summary of antiseizure medications available in the United States: 4th Edition," American Epilepsy Society, (Revised Apr. 1, 2024), 28 pages.

USE OF CANNABIDIOL IN THE TREATMENT OF SEIZURES ASSOCIATED WITH RARE EPILEPSY SYNDROMES RELATED TO GENETIC ABNORMALITIES

CROSS-REFERENCE TO RELATED APPLICATIONS

This application is a U.S. National Phase application, filed under 35 U.S.C. § 371(c), of International Application No. PCT/EP2021/069834, filed Jul. 15, 2021, which claims priority to, and the benefit of, United Kingdom Patent Application No. 2011127.4, filed Jul. 20, 2020. Each of these documents is incorporated by reference herein in its entirety for all purposes.

FIELD OF THE INVENTION

The present invention relates to the use of cannabidiol (CBD) for the treatment of seizures associated with rare epilepsy syndromes. In particular the seizures associated with rare epilepsy syndromes that are treated are those which are experienced in patients with PCDH19 mutation. In a further embodiment the types of seizures include tonic-clonic seizures. Preferably the dose of CBD is between 5 mg/kg/day to 50 mg/kg/day.

In a further embodiment the CBD used is in the form of a highly purified extract of *cannabis* such that the CBD is present at greater than 95% of the total extract (w/w) and the cannabinoid tetrahydrocannabinol (THC) has been substantially removed, to a level of not more than 0.15% (w/w).

Preferably the CBD used is in the form of a botanically derived purified CBD which comprises greater than or equal to 98% (w/w) CBD and less than or equal to 2% (w/w) of other cannabinoids. More preferably the other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w). The botanically derived purified CBD preferably also comprises a mixture of both trans-THC and cis-THC. Alternatively, a synthetically produced CBD is used.

Most preferably the other cannabinoids present are THC at a concentration of about 0.01% to about 0.1% (w/w); CBD-C1 at a concentration of about 0.1% to about 0.15% (w/w); CBDV at a concentration of about 0.2% to about 0.8% (w/w); and CBD-C4 at a concentration of about 0.3% to about 0.4% (w/w). Most preferably still the THC is present at a concentration of about 0.02% to about 0.05% (w/w).

Where the CBD is given concomitantly with one or more other anti-epileptic drugs (AED), the CBD may be formulated for administration separately, sequentially or simultaneously with one or more AED or the combination may be provided in a single dosage form.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "08i failure of adequate trials of two tolerated and appropriately chosen and used AED schedules (*whether as monotherapies or in combination*) *to achieve sustained seizure freedom*" (Kwan et al., 2009).

Individuals who develop epilepsy during the first few years of life are often difficult to treat and as such are often termed treatment resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification.

Generalized seizures, where the seizure arises within and rapidly engages bilaterally distributed networks, can be split into six subtypes: tonic-clonic (grand mal) seizures; absence (petit mal) seizures; clonic seizures; tonic seizures; atonic seizures and myoclonic seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace secondary generalized seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Epilepsy associated with PCDH19 mutation is a rare X-linked epilepsy syndrome characterized by early onset seizures, cognitive and sensory delays, and behavioral problems. It is caused by a mutation in the PCDH19 gene which codes for protocadherin 19, a protein that plays an important role in communication of brain cells.

Seizure onset is typically between 3 months to 3 years old and they may become less frequent in later childhood and adolescence. They tend to occur in clusters in the beginning and can vary significantly, with a duration of days to weeks in some children. Cognitive and intellectual disabilities can range from mild to severe. Despite seizure clusters some children may have normal development and cognitive function.

Other symptoms that may arise are aggression; attention problems; anxiety; OCD; autistic spectrum features; depression; psychosis. Symptoms noted in some children include fine and gross motor delays; language delay; sensory integration difficulties; sleep problems; low motor tone; constipation; apnea with seizures.

Seizure medication is the first line of treatment to prevent seizures and seizure clusters. However, the seizures are very difficult to control with medicines during the early years of life and may respond better to medicines over time. Vagal nerve stimulation may be considered in some cases.

Cannabidiol (CBD), a non-psychoactive derivative from the *cannabis* plant, has demonstrated anti-convulsant properties in several anecdotal reports, pre-clinical and clinical studies both in animal models and humans. Three randomized control trials showed efficacy of the purified pharmaceutical formulation of CBD in patients with Dravet and Lennox-Gastaut syndrome.

Based on these three trials, a botanically derived purified CBD preparation was approved by FDA in June 2018 for the treatment of seizures associated with Dravet and Lennox-Gastaut syndromes.

In 2018 an English newspaper reported on the use of *cannabis*-based medication to treat a child with PCDH19 mutation. However, the article does not indicate or even suggest the types of seizures that were reduced nor the composition of the *cannabis*-based medication.[1]

A 2019 article discloses the use of *cannabis* to treat a child with PCDH19 mutation.[2] The treatment consisted of a combination of two products, one that contained a relatively high THC concentration (14%) and another so-called CBD-only product (9% CBD).

Porter and Jacobson[3] reported on a case whereby a patient with Epilepsy in Females with Mental Retardation (EFMR), a condition caused by PCDH19 gene mutation, was treated with 7 mg/kg/day CBD in combination with a relatively high THC concentration of 0.5 mg/kg/day.

WO2019/045121 and WO2019/071302 disclose the coadministration of CBD with an additional therapy in the treatment of a range of epileptic syndromes, one of which listed is PCDH19 mutation. However, neither provide any evidence to demonstrate effectiveness in this particular epilepsy syndrome by the combination treatment, let alone the efficacy of CBD alone in this syndrome.

More generally, several publications[4-9] mention the use of CBD in the treatment of seizures associated with rare and refractory epilepsies. However, none of these disclosures contain any data of patients with PCDH19 mutation being successfully treated with highly purified CBD.

The applicant has found by way of an open label, expanded-access program that treatment with CBD resulted in a significant reduction in tonic-clonic seizures in a patient with PCDH19 mutation.

BRIEF SUMMARY OF THE DISCLOSURE

In accordance with a first aspect of the present invention there is provided a cannabidiol (CBD) preparation for use in the treatment of seizures associated with PCDH19 mutation.

In a further embodiment, the seizures associated with PCDH19 mutation are tonic-clonic seizures.

In a further embodiment, the CBD preparation comprises greater than 95% (w/w) CBD and not more than 0.15% (w/w) tetrahydrocannabinol (THC).

Preferably the CBD preparation comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

Preferably the CBD preparation is used in combination with one or more concomitant anti-epileptic drugs (AED).

Preferably the one or more AED is selected from the group consisting of: levetiracetam, clobazam, topiramate, gabapentin and phenytoin.

In one embodiment the CBD is present is isolated from *cannabis* plant material. Preferably at least a portion of at least one of the cannabinoids present in the CBD preparation is isolated from *cannabis* plant material.

In a further embodiment the CBD is present as a synthetic preparation. Preferably at least a portion of at least one of the cannabinoids present in the CBD preparation is prepared synthetically.

Preferably the dose of CBD is greater than 5 mg/kg/day. More preferably the dose of CBD is 20 mg/kg/day. More preferably the dose of CBD is 25 mg/kg/day. More preferably the dose of CBD is 50 mg/kg/day.

In accordance with a second aspect of the present invention there is provided a method of treating seizures associated with PCDH19 mutation comprising administering a cannabidiol (CBD) preparation to the subject in need thereof.

Definitions

Definitions of some of the terms used to describe the invention are detailed below:

Over 100 different cannabinoids have been identified, see for example, Handbook of *Cannabis*, Roger Pertwee, Chapter 1, pages 3 to 15. These cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoids" are defined as cannabinoids that have been extracted from the *cannabis* plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Tonic-clonic seizures" consist of two phases: the tonic phase and the clonic phase. In the tonic phase the body becomes entire rigid, and in the clonic phase there is uncontrolled jerking. Tonic-clonic seizures may or may not be preceded by an aura, and are often followed by headache, confusion, and sleep. They may last mere seconds or continue for several minutes. These seizures are also known as a grand mal seizure.

DETAILED DESCRIPTION

Preparation of Highly Purified CBD Extract

The following describes the production of the highly-purified (>95% w/w) cannabidiol extract which has a known and constant composition.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD. Although the CBD is highly purified because it is produced from a *cannabis* plant rather than synthetically there is a small number of other cannabinoids which are co-produced and co-extracted with the CBD. Details of these cannabinoids and the quantities in which they are present in the medication are as described in Table A below.

TABLE A

Composition of highly purified CBD extract

| Cannabinoid | Concentration |
|---|---|
| CBD | >95% w/w |
| CBDA | NMT 0.15% w/w |
| CBDV | NMT 1.0% w/w |

TABLE A-continued

Composition of highly purified CBD extract

| Cannabinoid | Concentration |
|---|---|
| $\Delta^9$ THC | NMT 0.15% w/w |
| CBD-C4 | NMT 0.5% w/w |

>—greater than
NMT—not more than

Preparation of Botanically Derived Purified CBD

The following describes the production of the botanically derived purified CBD which comprises greater than or equal to 98% w/w CBD and less than or equal to other cannabinoids was used in the open label, expanded-access program described in Example 1 below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (botanically derived purified CBD).

The plant starting material is referred to as Botanical Raw Material (BRM); the botanical extract is the intermediate; and the active pharmaceutical ingredient (API) is CBD, the drug substance.

All parts of the process are controlled by specifications. The botanical raw material specification is described in Table B and the CBD API is described in Table C.

TABLE B

CBD botanical raw material specification

| Test | Method | Specification |
|---|---|---|
| Identification: | | |
| A | Visual | Complies |
| B | TLC | Corresponds to standard (for CBD & CBDA) |
| C | HPLC/UV | Positive for CBDA |
| Assay: | In-house | NLT 90% of assayed |
| CBDA + CBD | (HPLC/UV) | cannabinoids by peak area |
| Loss on Drying | Ph. Eur. | NMT 15% |
| Aflatoxin | UKAS method | NMT 4 ppb |
| Microbial: | Ph. Eur. | NMT $10^7$ cfu/g |
| TVC | | NMT $10^5$ cfu/g |
| Fungi | | NMT $10^2$ cfu/g |
| *E. coli* | | |
| Foreign Matter: | Ph. Eur. | NMT 2% |
| Residual Herbicides and Pesticides | Ph. Eur. | Complies |

TABLE C

Specification of an exemplary botanically derived purified CBD preparation

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |

TABLE C-continued

Specification of an exemplary botanically derived purified CBD preparation

| Test | Test Method | Limits |
|---|---|---|
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| CBDA | HPLC-UV | NMT 0.15% w/w |
| CBDV | | 0.2-1.0% w/w |
| THC | | 0.01-0.1% w/w |
| CBD-C4 | | 0.3-0.5% w/w |
| Residual Solvents: | | |
| Alkane | GC | NMT 0.5% w/w |
| Ethanol | | NMT 0.5% w/w |
| Residual Water | Karl Fischer | NMT 1.0% w/w |

The purity of the botanically derived purified CBD preparation was greater than or equal to 98%. The botanically derived purified CBD includes THC and other cannabinoids, e.g., CBDA, CBDV, CBD-C1, and CBD-C4.

In some embodiments, the CBD preparation comprises not more than 0.15% THC based on total amount of cannabinoid in the preparation. In some embodiments, the CBD preparation comprises about 0.01% to about 0.1% THC based on total amount of cannabinoid in the preparation. In some embodiments, the CBD preparation comprises about 0.02% to about 0.05% THC based on total amount of cannabinoid in the preparation.

In some embodiments, the CBD preparation comprises about 0.2% to about 1.0% CBDV based on total amount of cannabinoid in the preparation. In some embodiments, the CBD preparation comprises about 0.2% to about 0.8% CBDV based on total amount of cannabinoid in the preparation.

In some embodiments, the CBD preparation comprises about 0.3% to about 0.5% CBD-C4 based on total amount of cannabinoid in the preparation. In some embodiments, the CBD preparation comprises about 0.3% to about 0.4% CBD-C4 based on total amount of cannabinoid in the preparation.

In some embodiments, the CBD preparation comprises about 0.1% to about 0.15% CBD-C1 based on total amount of cannabinoid in the preparation.

Distinct chemotypes of the *Cannabis sativa* L. plant have been produced to maximize the output of the specific chemical constituents, the cannabinoids. Certain chemovars produce predominantly CBD. Only the (−)-trans isomer of CBD is believed to occur naturally. During purification, the stereochemistry of CBD is not affected.

Production of CBD Botanical Drug Substance

An overview of the steps to produce a botanical extract, the intermediate, are as follows:

a) Growing
b) Direct drying
c) Decarboxylation
d) Extraction—using liquid $CO_2$
e) Winterization using ethanol
f) Filtration
g) Evaporation High CBD chemovars were grown, harvested, dried, baled and stored in a dry room until required. The botanical raw material (BRM) was finely chopped using an Apex mill fitted with a 1 mm screen. The milled BRM was stored in a freezer prior to extraction.

Decarboxylation of CBDA to CBD was carried out using heat. BRM was decarboxylated at 115° C. for 60 minutes.

Extraction was performed using liquid $CO_2$ to produce botanical drug substance (BDS), which was then crystalized to produce the test material. The crude CBD BDS was winterized to refine the extract under standard conditions (2 volumes of ethanol at −20° C. for approximately 50 hours). The precipitated waxes were removed by filtration and the solvent was removed to yield the BDS.

Production of Botanically Derived Purified CBD Preparation

The manufacturing steps to produce the botanically derived purified CBD preparation from BDS were as follows:

a) Crystallization using $C_5$-$C_{12}$ straight chain or branched alkane
b) Filtration
c) Vacuum drying The BDS produced using the methodology above was dispersed in $C_5$-$C_{12}$ straight chain or branched alkane. The mixture was manually agitated to break up any lumps and the sealed container then placed in a freezer for approximately 48 hours. The crystals were isolated via vacuum filtration, washed with aliquots of cold $C_5$-$C_{12}$ straight chain or branched alkane, and dried under a vacuum of <10 mb at a temperature of 60° C. until dry. The botanically derived purified CBD preparation was stored in a freezer at −20° C. in a pharmaceutical grade stainless steel container, with FDA food grade approved silicone seal and clamps.

Physicochemical Properties of the Botanically Derived Purified CBD

The botanically derived purified CBD used in the clinical trial described in the invention comprises greater than or equal to 98% (w/w) CBD and less than or equal to 2% (w/w) of other cannabinoids. The other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w).

The botanically derived purified CBD used additionally comprises a mixture of both trans-THC and cis-THC. It was found that the ratio of the trans-THC to cis-THC is altered and can be controlled by the processing and purification process, ranging from 3.3:1 (trans-THC:cis-THC) in its unrefined decarboxylated state to 0.8:1 (trans-THC:cis-THC) when highly purified.

Furthermore, the cis-THC found in botanically derived purified CBD is present as a mixture of both the (+)-cis-THC and the (−)-cis-THC isoforms.

Clearly a CBD preparation could be produced synthetically by producing a composition with duplicate components.

Example 1 below describes the use of a botanically derived purified CBD in an open label, expanded-access program to investigate the clinical efficacy and safety of purified pharmaceutical cannabidiol formulation (CBD) in the treatment of seizures associated with PCDH19 mutation.

Example 1: Clinical Efficacy and Safety of Purified Pharmaceutical Cannabidiol (CBD) in the Treatment of Patients with PCDH19 Mutation Study Design Subjects were required to be on one or more AEDs at stable doses for a minimum of two weeks prior to baseline and to have stable vagus nerve stimulation (VNS) settings and ketogenic diet ratios for a minimum of four weeks prior to baseline.

Patients were administered botanically derived purified CBD in a 100 mg/mL sesame oil-based solution.

A maximum dose of 50 mg/kg/day could be utilised for patients who were tolerating the medication but had not achieved seizure control; these patients had further weekly titration by 5 mg/kg/day.

There was one patient in this study, who received CBD for 16 weeks. Modifications were made to concomitant AEDs as per clinical indication.

Seizure frequency, intensity, and duration were recorded by caregivers in a diary during a baseline period of at least 28 days. Changes in seizure frequency relative to baseline were calculated after at least 2 weeks and at defined time-points of treatment.

Statistical Methods:

Patients may be defined as responders if they had more than 50% reduction in seizure frequency compared to baseline. The percent change in seizure frequency was calculated as follows:

$$\%\ \text{change seizure frequency} = \frac{\left(\begin{array}{c}\text{(weekly seizure frequency time interval)} - \\ \text{(weekly seizure frequency Baseline)}\end{array}\right)}{\text{(weekly seizure frequency Baseline)}} \times 100$$

The percent change of seizure frequency may be calculated for any time interval where seizure number has been recorded. For the purpose of this example the percent change of seizure frequency for the end of the treatment period was calculated as follows:

$$\%\ \text{reduction seizure frequency} = \frac{\left(\begin{array}{c}\text{(weekly seizure frequency Baseline)} - \\ \text{(weekly seizure frequency End)}\end{array}\right)}{\text{(weekly seizure frequency Baseline)}} \times 100$$

Results

Patient Description

One patient enrolled in the open label, expanded-access program had PCDH19 mutation. This patient experienced tonic-clonic seizures and was taking several concomitant AEDs.

The patient was 16 years old and she was female as detailed in Table 1 below.

TABLE 1

Patient demographics, seizure type and concomitant medication

| Patient Number | Age (years) | Sex | Seizure types | Concomitant AEDs |
|---|---|---|---|---|
| 1 | 16.20 | F | Tonic-clonic | CLB, LEV, TPM, GBP, PHT |

LEV = levetiracetam,
CLB = clobazam,
TPM = topiramate,
GBP = gabapentin,
PHT = phenytoin Study Medication and Concomitant Medications The patient on the study was titrated up to 25 mg/kg/day of CBD.

At the time of starting CBD the patient was on five concomitant AEDs.

Clinical Changes

Table 2 illustrates the seizure frequency for the patient as well as the dose of CBD given.

TABLE 2

Seizure frequency data for Patient 1
Patient 1

| Time | Seizure Type Tonic-clonic | Dose CBD (mg/kg/day) |
|---|---|---|
| Baseline | 280.0 | — |
| 4 weeks | 120.0 | 15.0 |
| 8 weeks | 160.0 | 25.0 |
| 16 weeks | 140.0 | 25.0 |

Patient 1 was treated for 16 weeks and experienced a 50% reduction in tonic-clonic seizures over the treatment period.

Overall, the patient reported a reduction of 50% in seizures over period of treatment with CBD. CBD was effective in reducing the frequency of tonic-clonic seizures.

CONCLUSIONS

These data indicate that CBD was able to significantly reduce the number of seizures associated with PCDH19 mutation. Clearly the treatment is of significant benefit in this difficult to treat epilepsy syndrome given the high response rate experienced in the patient.

In conclusion, this study signifies the use of CBD for treatment of seizures associated with PCDH19 mutation. Seizure types include tonic-clonic seizures for which seizure frequency rate decreased significantly, by 50%.

REFERENCES

1 Oppenheim. (2018) "Government refuses medical *cannabis* to six-year-old epileptic boy who had 3,000 seizures in a year." The Independent. https://www.independent.co.uk/news/uk/home-news/alfie-dingley-home-office-medical-cannabis-denies-seizures-netherlands-a8216596, html 2. Deacon (2019) "The fight for getting access to medical *cannabis* in the UK goes on." Health Europa. https://www.healtheuropa.eu/access-to-medical-cannabis-in-the-uk/93025/
3. Porter and Jacobson (2013) "Report of a parent survey of cannabidiol-enriched *cannabis* use in pediatric treatment-resistant epilepsy", pages 574-577. Epilepsy & Behavior, vol. 29, 2013
4. Kurian et al. (2018) "Focal cortical malformations in children with early infantile epilepsy and PCDH19 mutations: case report", pages 100-105. Dev. Med. Child Neurol., vol. 60, 2018
5. Hausman-Kedem et al. (2018) "Efficacy of CBD-enriched medical *cannabis* for treatment of refractory epilepsy in children and adolescents An observational, longitudinal study", pages 544-551. Brain and Development, vol. 40, 2018
6. Devinsky et al. (2017) "Trial of Cannabidiol for Drug-Resistant Seizures in the Dravet Syndrome", pages 2011-2020. N. Engl. J. Med., vol. 376, 2017
7. Hess et al. (2016) "Cannabidiol as a new treatment for drug-resistant epilepsy in tuberous sclerosis complex." Epilepsia, vol. 57, 2016
8. Thiele et al. (2019) "Cannabidiol in patients with Lennox-Gastaut syndrome: Interim analysis of an open-label extension study", pages 419-428. Epilepsia, vol. 60, 2019
9. Rosenberg et al. (2018) "Quality of Life of Childhood Epilepsy (QOLCE) in pediatric patients enrolled in a prospective, open label clinical study with cannabidiol (CBD)." pages 96-100. Epilepsia, vol. 58, 2018

The invention claimed is:

1. A method of treating seizures associated with a PCDH19 mutation in a patient in need thereof comprising administering a cannabidiol (CBD) drug substance to the patient in need thereof, wherein the CBD drug substance comprises greater than 95% (w/w) CBD and not more than 0.15% (w/w) tetrahydrocannabinol (THC).

2. The method of claim 1, wherein the seizures associated with a PCDH19 mutation are tonic-clonic seizures.

3. The method of claim 1, wherein the CBD drug substance comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

4. The method of claim 1, comprising administering the CBD drug substance in combination with one or more concomitant anti-epileptic drugs (AED).

5. The method of claim 4, wherein the one or more AED is selected from the group consisting of: levetiracetam, clobazam, topiramate, gabapentin and phenytoin.

6. The method of claim 1, wherein the CBD is present is isolated from *cannabis* plant material.

7. The method of claim 1, wherein at least a portion of at least one of the cannabinoids present in the CBD drug substance is isolated from *cannabis* plant material.

8. The method of claim 1, wherein the CBD is present as a synthetic drug substance.

9. The method of claim 8, wherein at least a portion of at least one of the cannabinoids present in the CBD drug substance is prepared synthetically.

10. The method of claim 1, wherein the dose of CBD is greater than 5 mg/kg/day.

11. The method of claim 1, wherein the dose of CBD is 20 mg/kg/day.

12. The method of claim 1, wherein the dose of CBD is 25 mg/kg/day.

13. The method of claim 1, wherein the dose of CBD is 50 mg/kg/day.

* * * * *